US 8,795,215 B2

(12) United States Patent
Rossi

(10) Patent No.: US 8,795,215 B2
(45) Date of Patent: Aug. 5, 2014

(54) ADJUSTABLE ORTHOPAEDIC CORSET FOR SPINAL COLUMN SUPPORT

(75) Inventor: Paolo Rossi, Stansstad (NW) (CH)

(73) Assignee: Orthoservice AG, Stansstad (CH)

( * ) Notice: Subject to any disclaimer, the term of this patent is extended or adjusted under 35 U.S.C. 154(b) by 126 days.

(21) Appl. No.: 13/423,387

(22) Filed: Mar. 19, 2012

(65) Prior Publication Data

US 2012/0245501 A1    Sep. 27, 2012

(30) Foreign Application Priority Data

Mar. 24, 2011   (IT) .............................. MI2011A0461

(51) Int. Cl.
  *A61F 5/00*          (2006.01)
(52) U.S. Cl.
  USPC ................................. 602/19; 602/5
(58) Field of Classification Search
  USPC ........ 602/19, 5; 2/45; 128/96.1, 100.1, 101.1, 128/99.1
  See application file for complete search history.

(56) References Cited

U.S. PATENT DOCUMENTS

| | | | | | |
|---|---|---|---|---|---|
| 2,828,737 | A | * | 4/1958 | Hale | 602/19 |
| 3,282,264 | A | * | 11/1966 | Connelly | 602/19 |
| 7,662,121 | B2 | * | 2/2010 | Zours | 602/19 |
| 2010/0318010 | A1 | | 12/2010 | Sandifer et al. | |

FOREIGN PATENT DOCUMENTS

| | | |
|---|---|---|
| WO | WO 2007/043079 A1 | 4/2007 |
| WO | WO 2009/052031 A1 | 4/2009 |

OTHER PUBLICATIONS

Italian Search Report issued on Nov. 2, 2011 in corresponding Italian Application No. MI 2011A 000461 filed on Mar. 24, 2011 (with an English Translation of Categories).

* cited by examiner

*Primary Examiner* — Kim M Lewis
(74) *Attorney, Agent, or Firm* — Oblon, Spivak, McClelland, Maier & Neustadt, L.L.P.

(57) ABSTRACT

An adjustable orthopedic corset to support a user's spinal column includes a rigid frame having a pair of upper, intermediate, and lower connecting slots to which a pair of front and rear straps, wrapped around the user, are connected. A further pair of connecting slots for a pair of pelvic straps, which join at the front of the user via abdominal plates, are envisaged at a lower end of the rigid frame. The pair of front and rear straps are provided by three sliding points for each side of the rigid frame. Each front strap is equipped with a first sliding point located at upper connecting slots. Each rear strap is equipped with an anchoring point located at the intermediate connecting slots, a second sliding point at slots secured to the lower ends of the two front straps, and a third sliding point at the lower connecting slots.

12 Claims, 10 Drawing Sheets

ADJUSTABLE ORTHOPAEDIC CORSET FOR SPINAL COLUMN SUPPORT

TECHNICAL FIELD

This invention relates to an adjustable orthopaedic corset for spinal column support, particularly for use in treating joint problems of the back or osteoporosis.

BACKGROUND

In the presence of certain pathologies both degenerative and inflammatory and also of traumatic origin of the spinal column or the torso, or even in the case of certain orthopaedic problems, it is known the use of particular braces of the type with corset, also known as "orthoses". These braces can be used, for example, to treat osteoporosis and guarantee a certain support for the patient, by absorbing the most intense stresses that affect the spinal column. These braces support the patient's torso resulting in a tendential reduction in kyphosis caused by osteoporosis.

There are currently various types of orthopaedic corsets that support or contain the torso. Said orthopaedic corsets generally comprise an extended rigid frame that is typically manufactured in a metal material, in a shape that is suitable for adhering to the spinal column. The rigid frame is configured to be secured, in a suitable position, on the patient's torso by fastening devices commonly of the strap variety.

The strap fastening devices comprise harnesses, the ends of which hook onto the rigid frame, and are wrapped around the body to which they are secured by suitable adjustable fastening means.

Certain embodiments of the orthopaedic corsets of the prior art are illustrated, by way of example, in documents EP-A-0917864, EP-A-1902691, EP-A-1962747, EP-A-2200545 and WO-A-2009/7017499. Said orthopaedic corsets of the prior art are not however free of drawbacks, including a certain difficulty that arises on wearing the orthopaedic corset and in carrying out the subsequent adjustments, but above all a certain inefficiency of the tensioning system.

SUMMARY

The aim of this invention is therefore the creation of an adjustable orthopaedic corset for spinal column support, that can be used in particular to treat joint problems of the back or osteoporosis, and which overcomes the aforementioned drawbacks of the prior art in an especially functional manner.

In detail, one aspect of this invention is the creation of an orthopaedic corset for spinal column support that can be easily, precisely and safely adjusted to meet the needs of both the patient and the orthopaedic technician.

Another aspect of the invention is the creation of an adjustable orthopaedic corset for spinal column support that causes as little inconvenience as possible to the patient wearing it.

A further aim of this invention is the creation of an adjustable orthopaedic corset for spinal column support that can be easily disassembled, for washing, for example.

These and other aspects of this invention are achieved by creating an adjustable orthopaedic corset for supporting the spinal column, particularly for use in treating joint problems of the back or osteoporosis.

Further characteristic of the invention are highlighted in the relevant claims, which are an integral part of the present description.

BRIEF DESCRIPTION OF THE DRAWINGS

The characteristics and the benefits of an adjustable orthopaedic corset for spinal column support according to the present invention will be clearer in the description that follows, provided by way of non-limiting example, with reference to the attached drawings, wherein.

DETAILED DESCRIPTION

The figures show an adjustable orthopaedic corset according to the invention, that is indicated as a whole with the reference number 10 and suitable to be used for supporting the spinal column of a patient.

The orthopaedic corset 10 comprises a rigid frame 14 contained in a pocket-shaped dorsal element 12 that is typically made of a soft fabric having a vertically extended shape and dimensions that allow said rigid frame 14 to be contained. Alternatively or additionally, the rigid frame 14 can be equipped with dorsal padding to protect the user's body from direct contact with said rigid frame 14.

Figure 1:
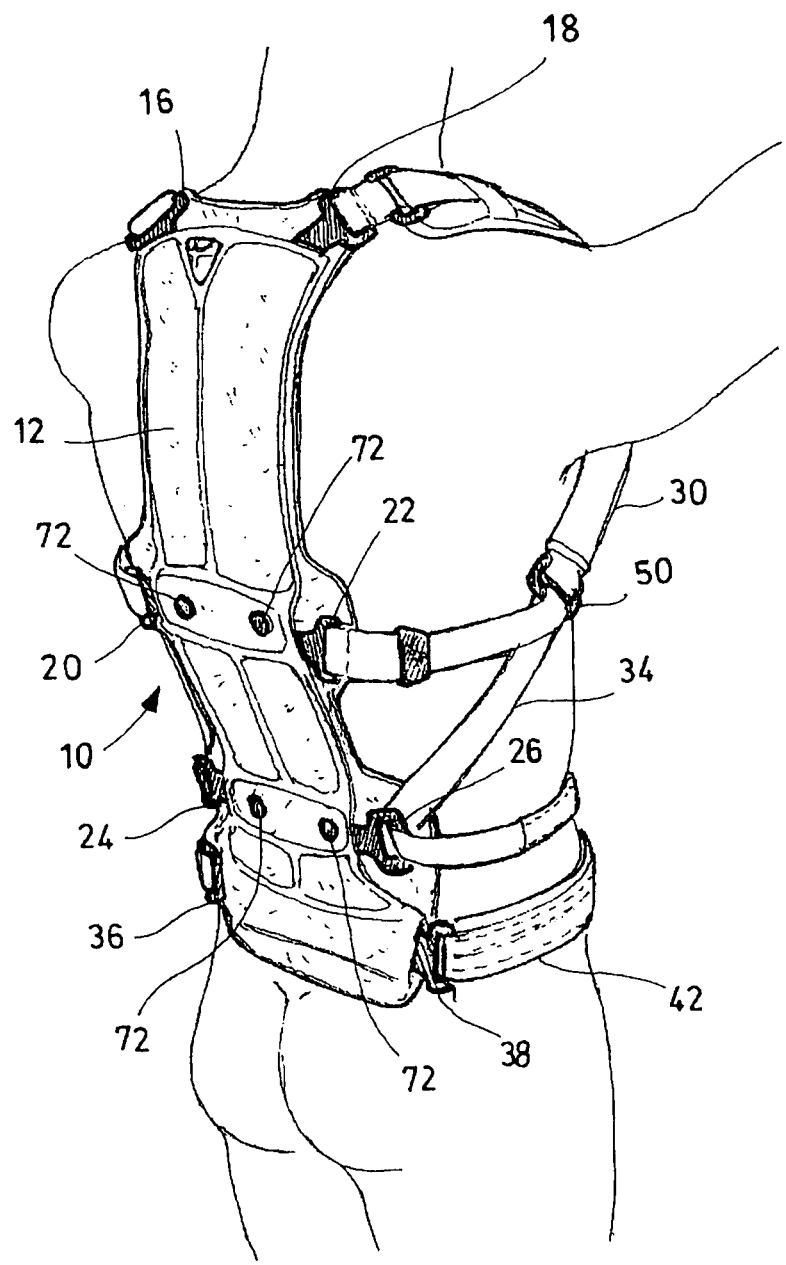
FIG. 1 is a perspective rear view of the adjustable orthopaedic corset for spinal column support according to the invention, when worn.
Figure 2:
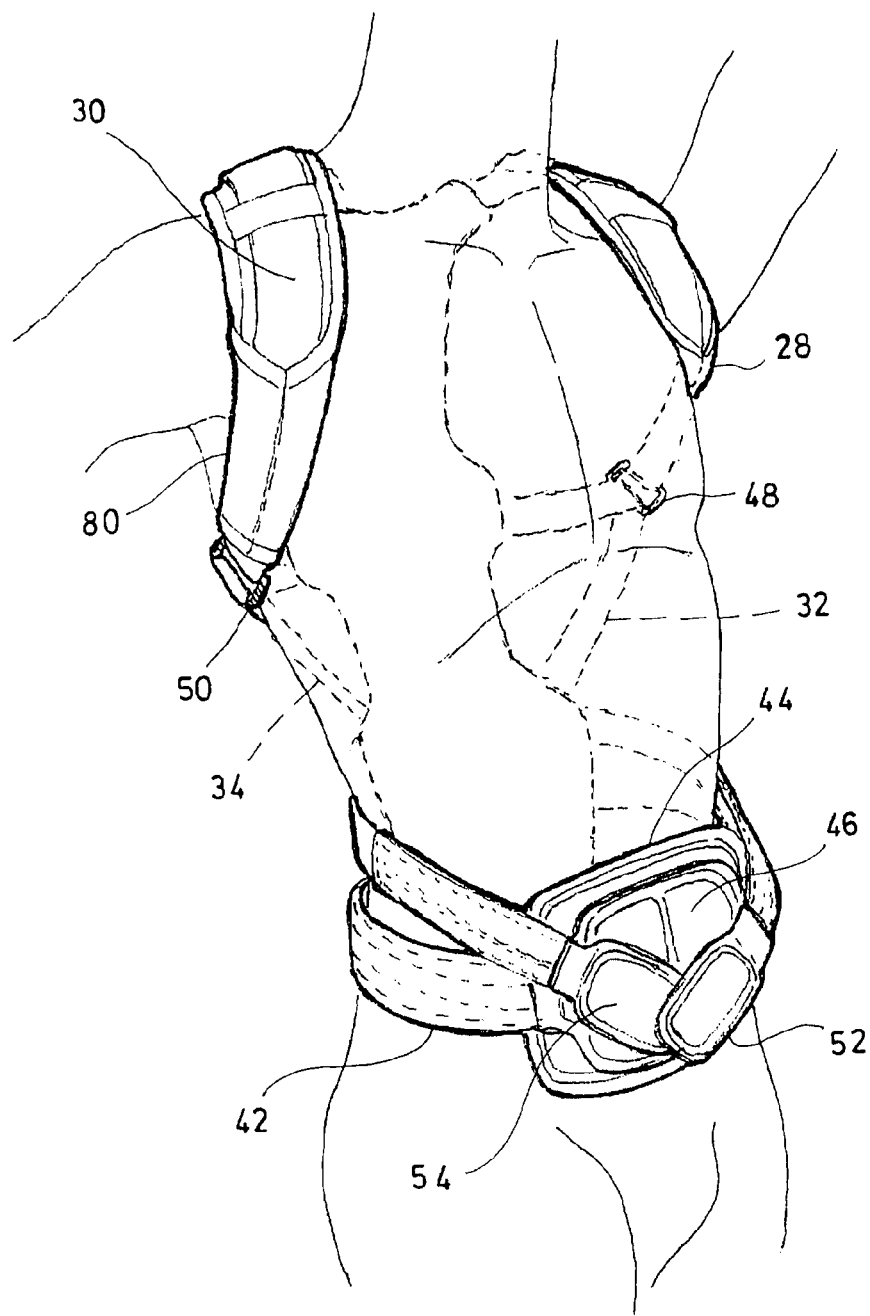
FIG. 2 is a perspective front view of the adjustable orthopaedic corset in FIG. 1.
Figure 3:
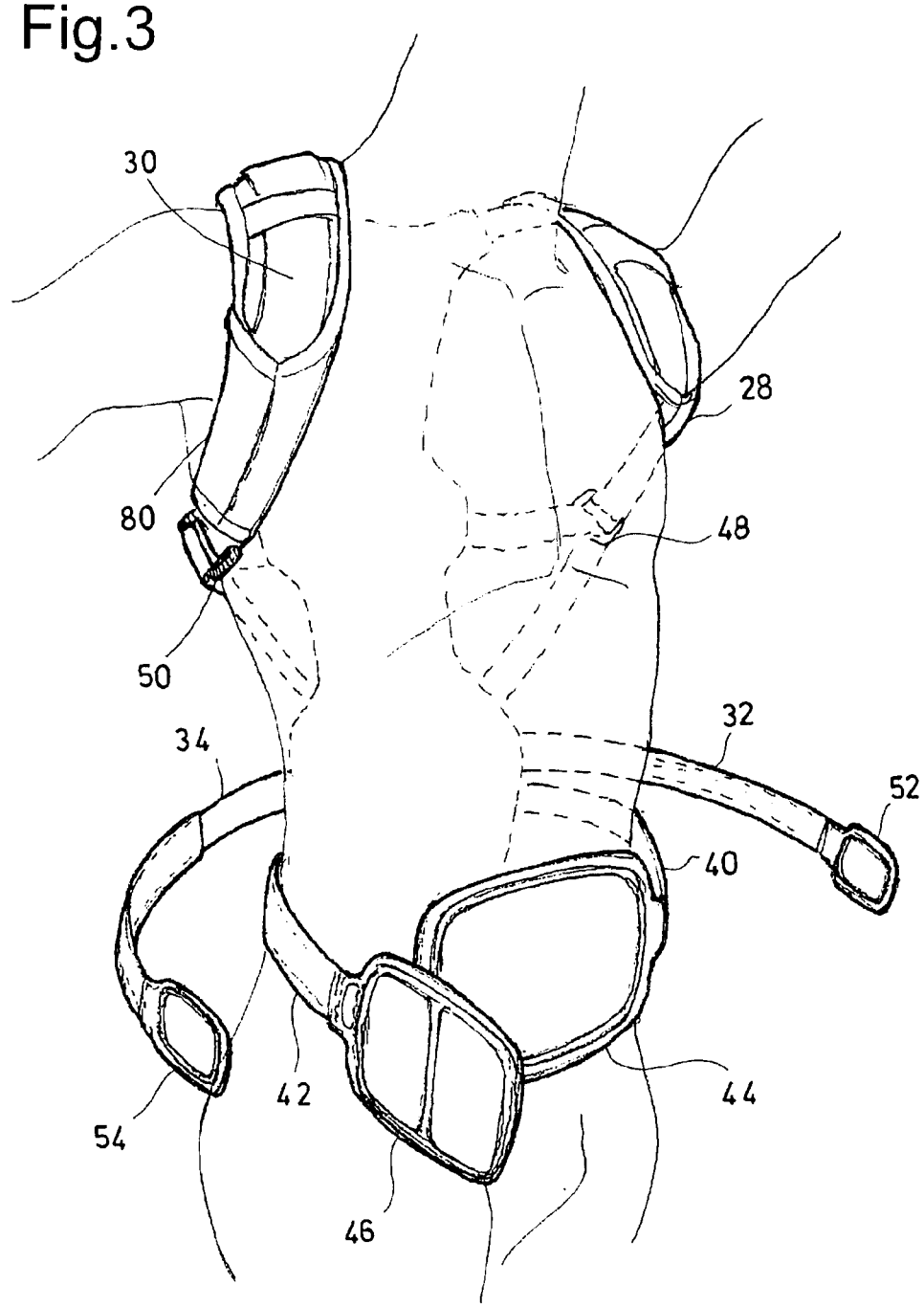
FIG. 3 is another perspective front view of the adjustable orthopaedic corset in FIG. 1, when open.
Figure 4:
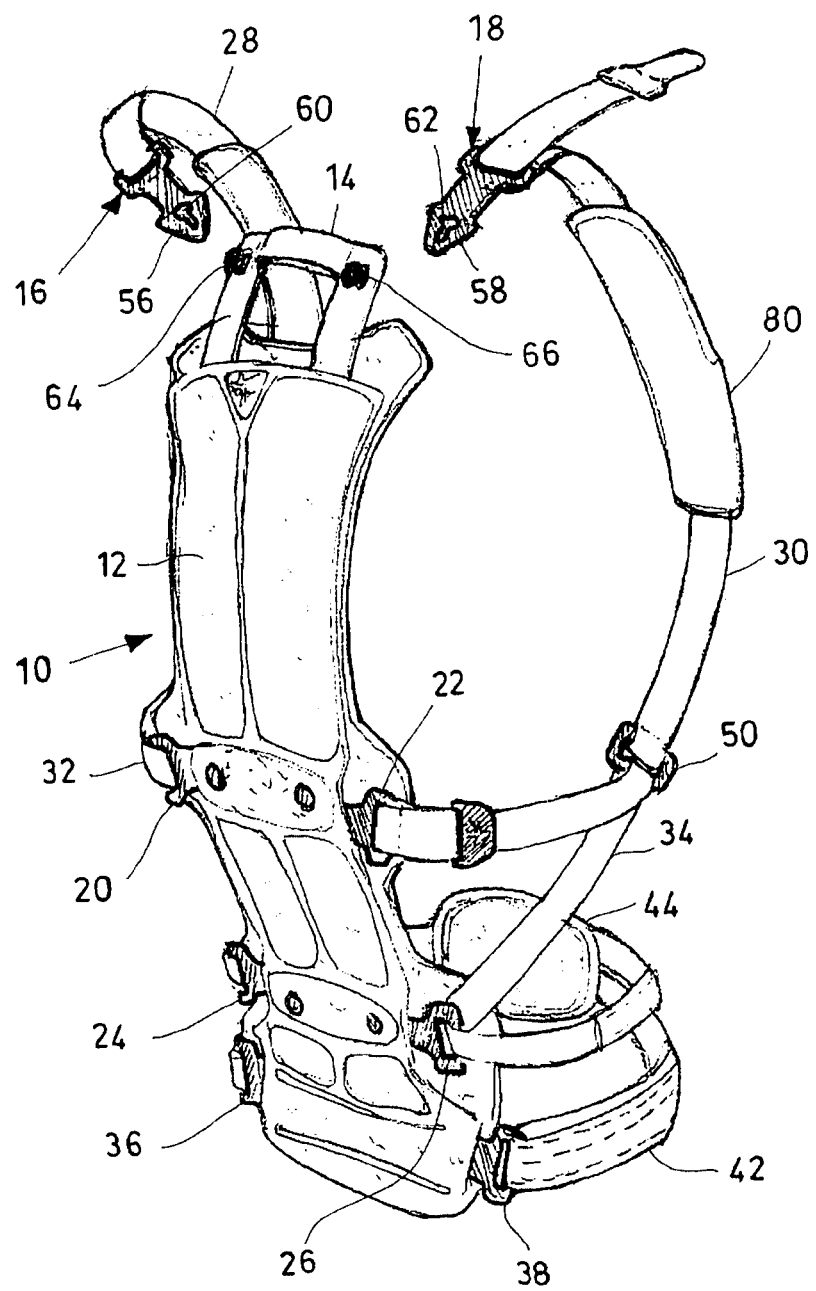
FIG. 4 is a perspective rear view of the adjustable orthopaedic corset in FIG. 1, when unworn.
Figure 5:
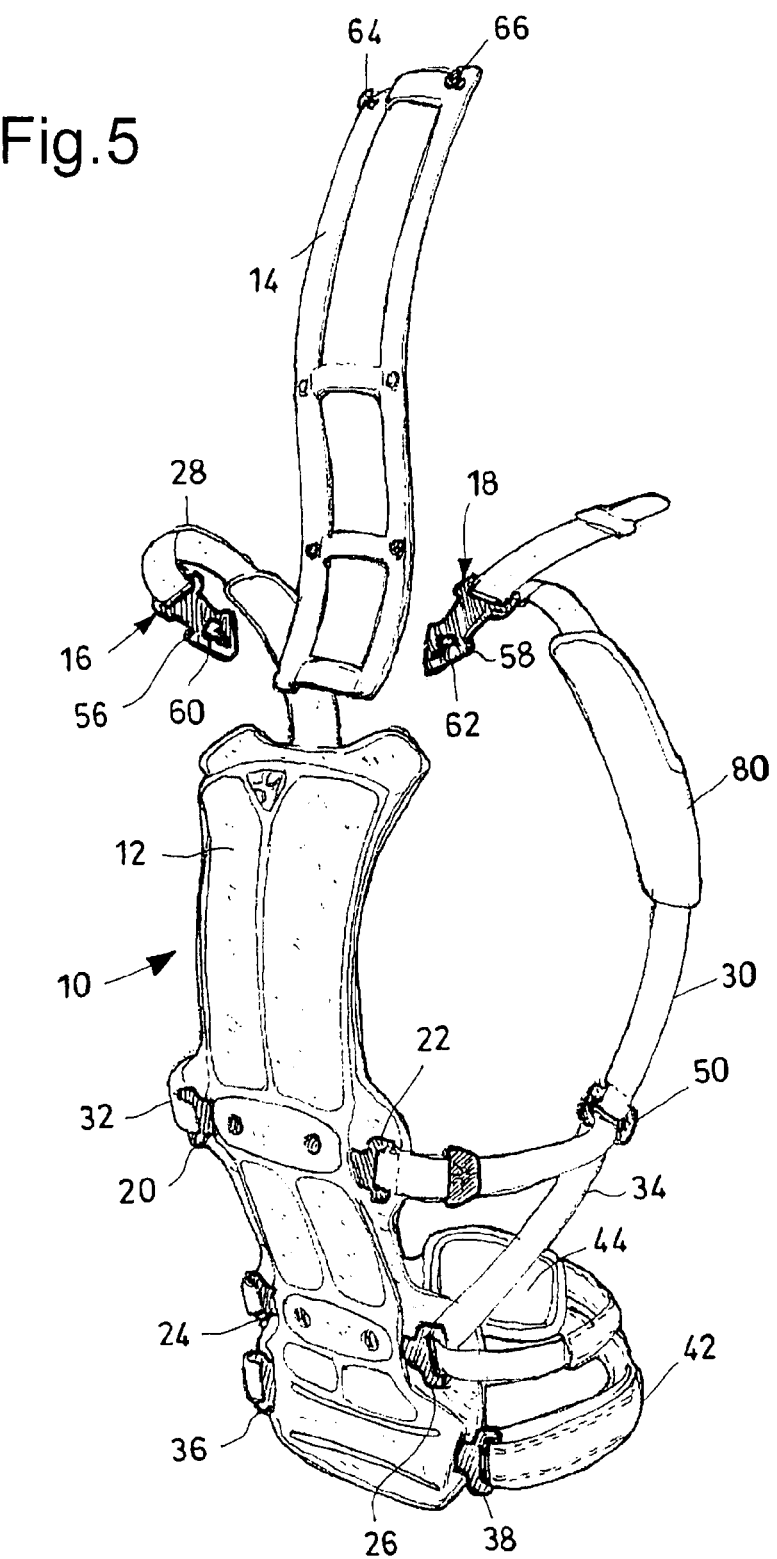
FIG. 5 is another perspective rear view of the adjustable orthopaedic corset in FIG. 1, when unworn and with the rigid frame completely undone.

The rigid frame 14, typically made of metal material or from a mouldable material that is sufficiently rigid and resistant for spinal column support, can be detached from the pocket-shaped dorsal element 12 (FIG. 5) and has an extended, curvilinear shape that follows the anatomical shape of the torso.

The rigid frame 14 has a plurality of connecting slots, positioned at points that are specularly symmetrical to said rigid frame 14, for a series of fastening straps that secure the orthopaedic corset 10 to the user's torso. The dorsal pocket-shaped element 12 is therefore equipped with a number of openings that corresponds to the number of connecting slots secured to the rigid frame 14, so as to allow said connecting slots to come out of the relevant openings to correctly connect the fastening straps.

More specifically, a pair of upper connecting slots 16, 18, a pair of intermediate connecting slots 20, 22 and a pair of lower connecting slots 24, 26, to which a pair of front straps 28, 30 are directly or indirectly operationally connected, which are wrapped around the user's shoulders, and a pair of rear straps 32, 34 that are wrapped around the user's sides, are envisaged.

A further pair of connecting slots 36, 38 is envisaged for a respective pair of pelvic straps 40, 42 at the inferior end of the rigid frame 14. The pelvic straps 40, 42 are joined at the front part of the user's abdomen by means of the respective superimposable abdominal plates or "pads" 44, 46, that are essentially quadrilateral and suitable for being wrapped around the pubic area when the orthopaedic corset 10 is worn by the user. The abdominal pads 44, 46 are joined by Velcro fasteners.

According to the invention, the fastening straps of the orthopaedic corset 10, i.e. the pair of front straps 28, 30 for the shoulders and the pair of rear straps 32, 34 for the sides, are equipped with three separate sliding points for each side of the pocket-shaped dorsal element 12. More specifically, each front strap 28 or 30 is provided with a first sliding point at the respective upper connecting slots 16, 18, whereas each rear strap 32, 34 is provided with an anchoring point at the respective intermediate connecting slots 20, 22, a second sliding point at the slots 48, 50 respectively constrained to the lower ends of the two front straps 28, 30, and a third sliding point at the respective lower connecting slots 24, 26.

The inferior ends of the two rear straps 32, 34 are set up to hook onto the abdominal pads 44, 46 of the pelvic straps 40, 42. In detail, the inferior ends of the two rear straps 32, 34 are equipped with respective connecting plates or pads 52, 54 that connect one to the other and/or to the abdominal pads 44, 46 through closing means of the Velcro type.

Figure 6:
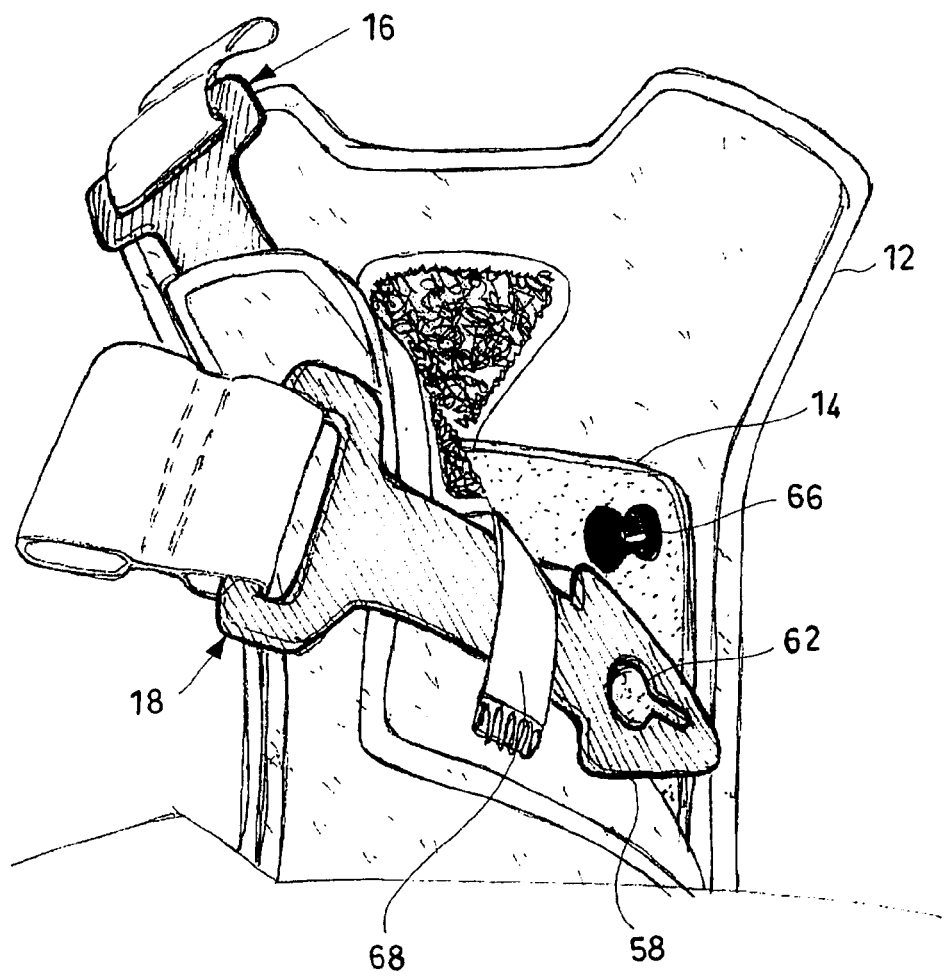
FIGS. 6 and 7 are detailed views of a detail of the adjustable orthopaedic corset in FIG. 1.
Figure 7:
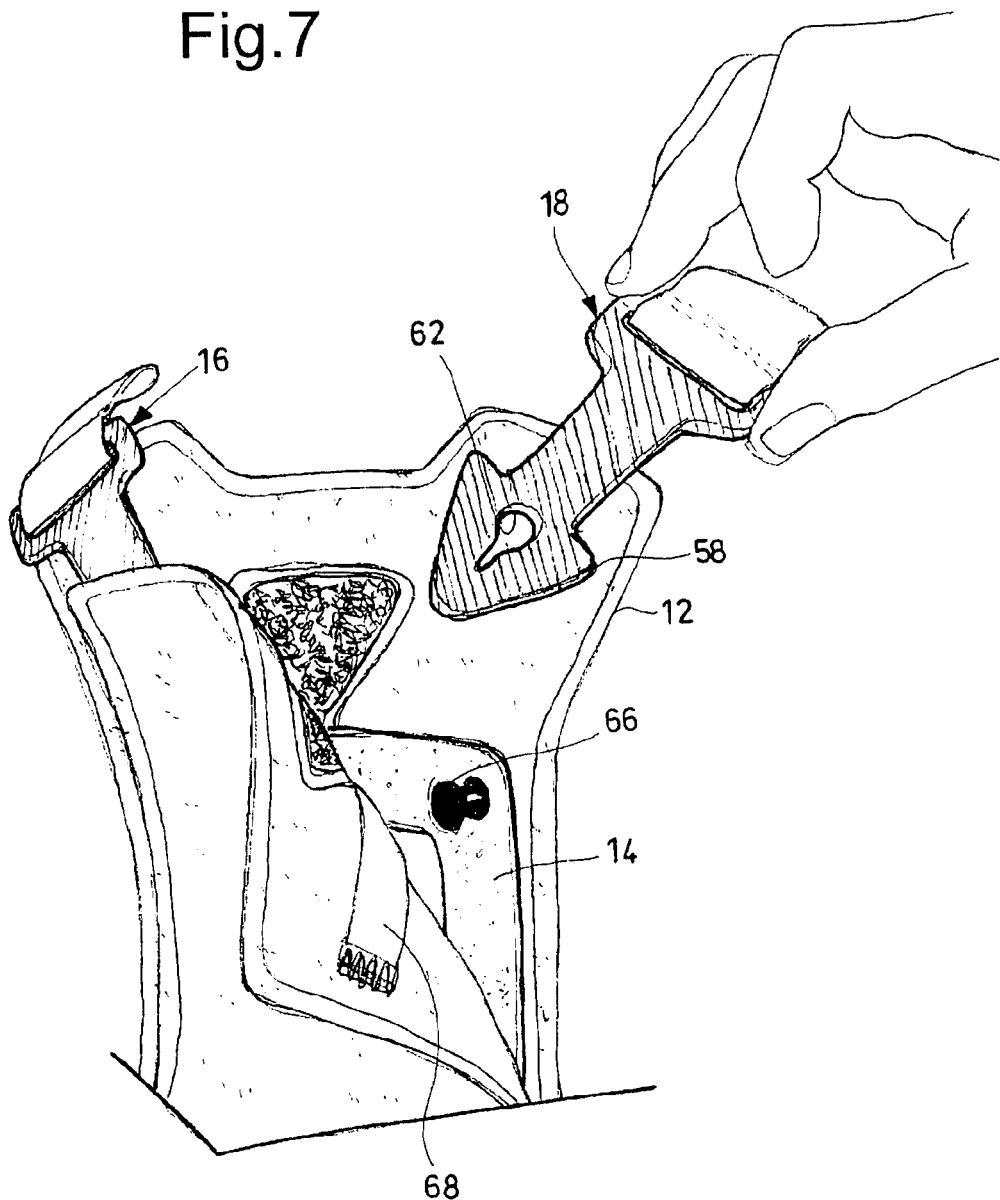
Figure 8:
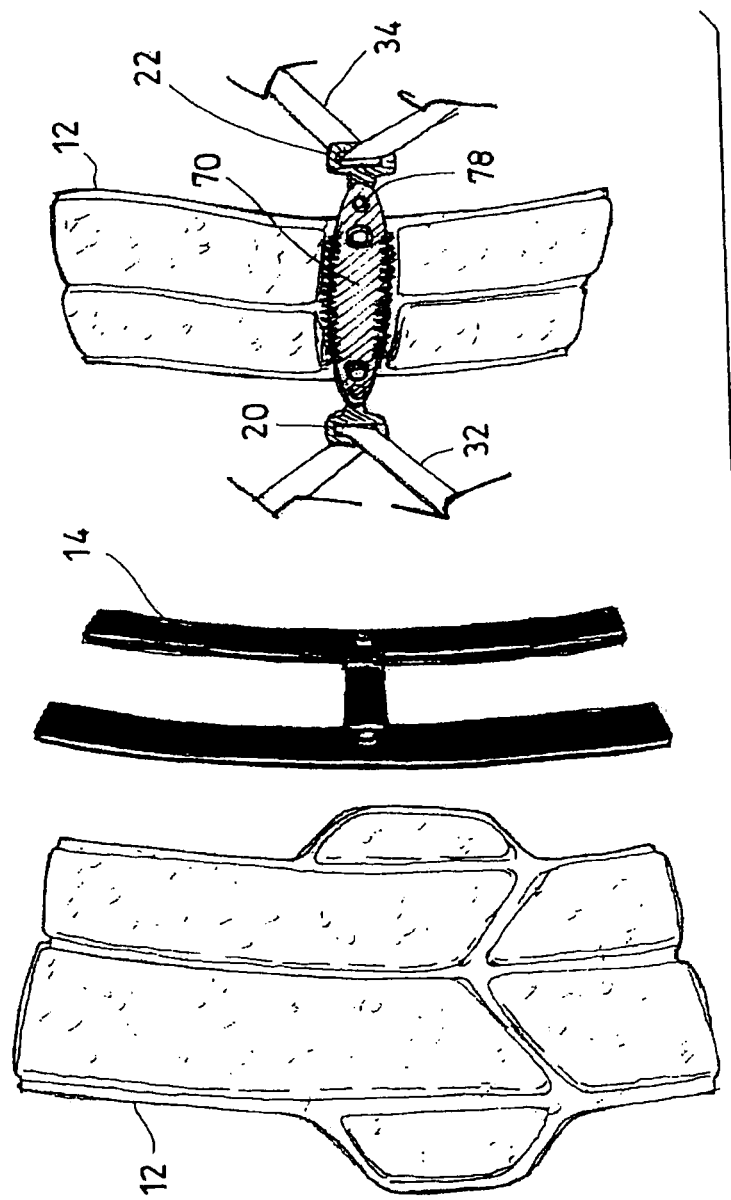
FIG. 8 is an exploded view of certain components of the adjustable orthopaedic corset in FIG. 1.
Figure 9:
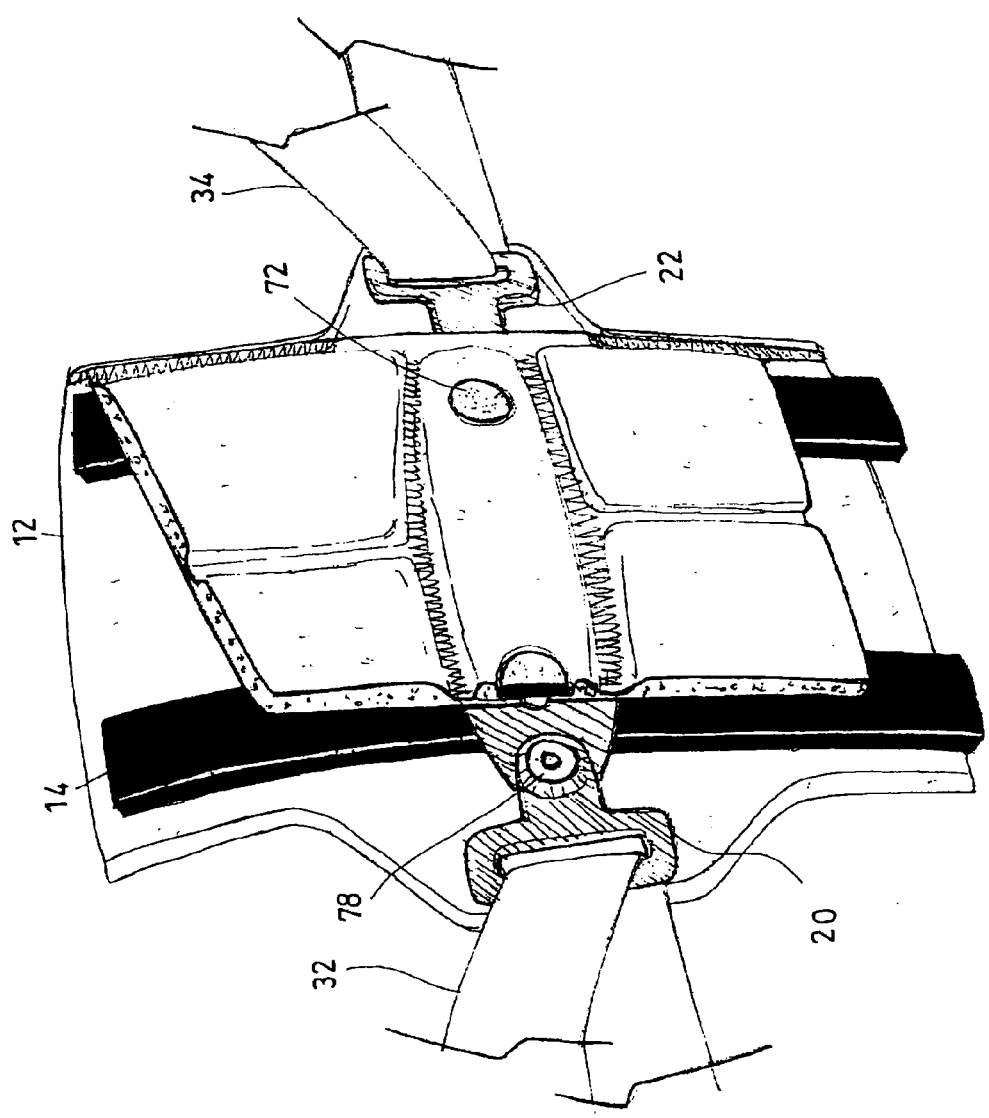
FIG. 9 is a partial section view of the components shown in FIG. 8.

The pair of upper connecting slots 16, 18 is equipped with a special type of connection that can easily be detached from the rigid frame 14. As shown in FIGS. 6 and 7, each upper connecting slot 16, 18 is equipped with a respective shaft 56, 58 which has a tapered through-hole 60, 62. Each through-hole 60, 62 allows the insertion therein and the blocking in position, in a reversible way, of a respective mushroom-shaped protruding pin element (64, 66) integral with the rigid frame (14). To simplify both the securing of the upper connecting slots 16, 18 to the rigid frame 14 and the blocking in position of said upper connecting slots 16, 18, once connected, the dorsal pocket-shaped element 12 is equipped with a pair of securing strips 68 (only one of which is shown in FIGS. 6 and 7), into which the respective shafts 56, 58 of the upper connecting slots 16, 18 are inserted.

Figure 10:
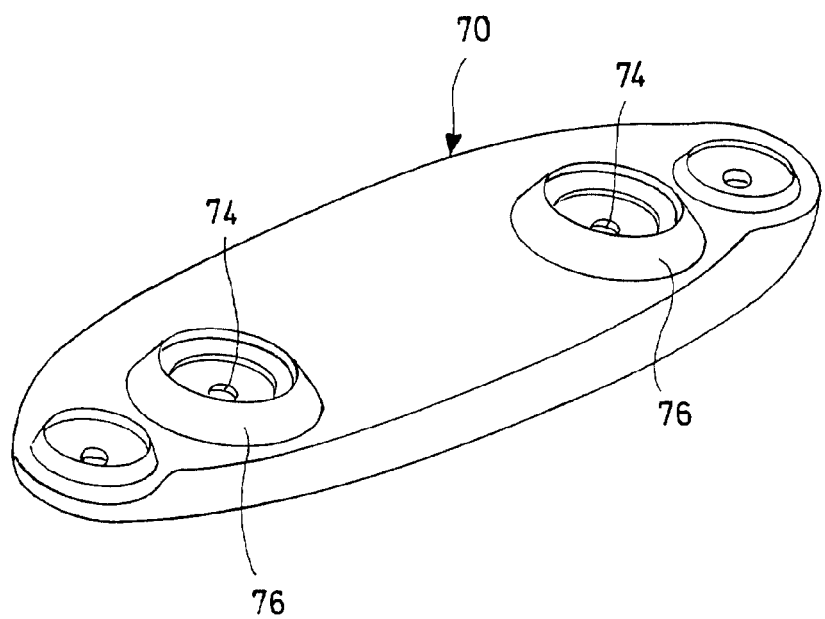
FIG. 10 is an enlarged view of a component of the adjustable orthopaedic corset in FIG. 1.

Also the two pairs of intermediate 20, 22 and lower 24, 26 connecting slots can be equipped with a second type of connection that is easily detached from the rigid frame 14. In detail, both the intermediate pair of connecting slots 20, 22 and the lower pair of connecting slots 24, 26 are secured, with rivets 78 for example, to a respective plate 70 (FIG. 10) that can be attached to the rigid frame 14 with press buttons 72 secured to a wall of the pocket-shaped dorsal element 12. Each plate 70 may be provided, at the holes 74 into which the press-buttons 72 are inserted, with inclined portions 76 to guide the press-buttons 72 into the correct position.

Lastly, the two connecting slots 36, 38 for the pelvic straps 40, 42 can be secured to the pocket-shaped dorsal element 12 rather than the rigid frame 14 by stitching.

The front straps 28, 30 for the shoulders can be equipped with padding 80 to ensure increased comfort to the user of the orthopaedic corset 10. On the other hand, the rear straps 32, 34 for the sides can be equipped with strips of elastic material at the relevant anchoring points of the intermediate connecting slots 20, 22.

The steps for the application of the orthopaedic corset 10 comprise in first of all placing the pocket-shaped dorsal element 12, containing the rigid frame 14 onto the user's back, while ensuring that the pair of front straps 28, 30 are resting on the user's shoulders. The pelvic straps 40, 42 must be wrapped around the sides of the user where they are then connected, at the front of the abdomen, by means of the respective superimposable abdominal pads 44, 46. Both the front straps 28, 30 for the shoulders and the pelvic straps 40, 42 can be adjusted in length and secured in the desired position by means of Velcro fasteners.

At this point the rear straps 32, 34 for the sides must be pulled so as to ensure that the rigid frame 14 is in constant contact with the spinal column. Pulling of the rear straps 32, 34 for the sides is extremely easy, thanks to the many sliding points, as is simple the securing thereof in the desired position, thanks to the abdominal connecting pads 52, 54 that are equipped with Velcro fasteners.

The specific layout of the sliding points of the front straps 28, 30 and the rear straps 32, 34 allows said straps to be horizontally or diagonally placed on the torso, thus preventing the orthopaedic corset 10 any possibility of sliding vertically.

In acting as a fixing point for both the pelvic straps 40, 42 and for the rear straps 32, 24 for the sides, the abdominal pads 44, 46, thus simplify adjustment operations of the orthopaedic corset 10.

Lastly, it should be noted that the presence of elements that can easily be detached, without any need for specific equipment, makes the orthopaedic corset 10 particularly simple to repair, wash and/or reconfigure.

It has thus been seen that the adjustable orthopaedic corset for spinal column support according to this invention achieves the aims as set out above.

A number of modification and changes can in any case be made to the adjustable orthopaedic corset thus devised for spinal column support according to the present invention, all of which fall within its creative design; in addition, all the details can be replaced by technically equivalent elements. In practice, any materials and any shapes and dimensions, can be used depending on the technical requirements.

The scope of protection of the invention is therefore defined by the accompanying claims.

The invention claimed is:
1. An adjustable orthopaedic corset for supporting a spinal column of a user, comprising:
   an extended and curvilinear rigid frame including, in points placed in specularly symmetric areas,
      a couple of upper connecting slots,
      a couple of front straps operatively connected respectively, directly or indirectly, to the couple of upper connecting slots,
      a couple of intermediate connecting slots,
      a couple of lower connecting slots,
      a couple of rear straps operatively connected respectively, directly or indirectly, to the couple of intermediate connecting slots and to the couple of lower connecting slots,
      a couple of base connecting slots, and
      a couple of pelvic straps attached respectively to the couple of base connecting slots that join, in a front part of the corset, by means of respective superimposed abdominal plates,
   wherein the couple of front straps and the couple of rear straps include three distinct sliding points for each side of the rigid frame,
   wherein each front strap includes a first sliding point at the respective upper connecting slots, and
   wherein each rear strap includes
      an anchoring point at the respective intermediate connecting slots,
      a second sliding point at joining slots, which are respectively constrained to lower ends of the couple of front straps, and
      a third sliding point at the respective lower connecting slots.
2. The adjustable orthopaedic corset according to claim 1, wherein the rigid frame is contained in a pocket-shaped dorsal element, having a vertical extended shape, and is releasable as regards said pocket-shaped dorsal element.

3. The adjustable orthopaedic corset according to claim 2, wherein lower ends of the couple of rear straps include respective attaching plates that are attachable on the abdominal plates of the pelvic straps.

4. The adjustable orthopaedic corset according to claim 3, further comprising a fabric hook and loop closing means via which the abdominal plates join together and via which the attaching plates join together with or without the abdominal plates.

5. The adjustable orthopaedic corset according to claim 2, wherein the couple of the upper connecting slots include respective shafts, each of which has a through-hole, having a tapered shape that allows insertion therein and blocking in position, in a reversible way, of a respective protruding pin element, which pin element is integral with the rigid frame, thereby permitting a connection that is easily loosened with respect to said rigid frame.

6. The adjustable orthopaedic corset according to claim 5, wherein the pocket-shaped dorsal element includes a couple of constraining strips, and
wherein the respective shafts of the upper connecting slots insert into the couple of constraining strips, so as to simplify a connection of said upper connecting slots to the rigid frame and to keep in position of said upper connecting slots once connected.

7. The adjustable orthopaedic corset according to claim 5, wherein both the intermediate couple of connecting slots, and the couple of lower connecting slots are constrained to a respective plate fixable to the rigid frame by means of pressing buttons constrained to a wall of the pocket-shaped dorsal element.

8. The adjustable orthopaedic corset according to claim 7, wherein on each plate, at holes in which the pressing buttons insert, inclined portions are disposed to ensure correct positioning of said pressing buttons.

9. The adjustable orthopaedic corset according to claim 5, wherein the couple of base connecting slots for the pelvic straps is constrained by means of a sewing to the pocket-shaped dorsal element.

10. The adjustable orthopaedic corset according to claim 1, wherein the rear straps include, at corresponding anchoring points to the intermediate connecting slots, strips made of elastic material.

11. The adjustable orthopaedic corset according to claim 1, wherein the rigid frame includes a dorsal padding for protection of a body of the user from direct contact with said rigid frame.

12. The adjustable orthopaedic corset according to claim 1, wherein the rigid frame is manufactured with a metallic material, or with a rigid and resistant moldable material so as to sustain the spinal column.

* * * * *